US009072651B1

(12) United States Patent
Parker, Jr.

(10) Patent No.: US 9,072,651 B1
(45) Date of Patent: Jul. 7, 2015

(54) PERSONAL APPARATUS FOR SEXUAL STIMULATION

(71) Applicant: Renworth Inc., Panama City (PA)

(72) Inventor: Michael H. Parker, Jr., Dominical (CR)

(73) Assignee: Renworth Inc., Panama (PA)

( * ) Notice: Subject to any disclaimer, the term of this patent is extended or adjusted under 35 U.S.C. 154(b) by 0 days.

(21) Appl. No.: 14/490,861

(22) Filed: Sep. 19, 2014

(51) Int. Cl.
*A61F 5/00* (2006.01)
*A61H 19/00* (2006.01)

(52) U.S. Cl.
CPC .................................... *A61H 19/00* (2013.01)

(58) Field of Classification Search
CPC ....... A61H 19/44; A61H 19/50; A61H 23/00; A61H 2201/1664; A61H 2201/1253; A61H 2201/164
USPC ....... 600/38–41; 601/97, 84; 606/201; 7/168, 7/170
See application file for complete search history.

(56) References Cited

U.S. PATENT DOCUMENTS

| | | | | |
|---|---|---|---|---|
| 3,301,553 | A * | 1/1967 | Brakeman | 482/119 |
| 4,500,136 | A * | 2/1985 | Murphy et al. | 297/284.9 |
| 4,722,327 | A * | 2/1988 | Harvey | 601/97 |
| 4,790,296 | A * | 12/1988 | Segal | 601/97 |
| 5,065,739 | A * | 11/1991 | Forrest et al. | 600/230 |
| 5,877,699 | A * | 3/1999 | Sharpe et al. | 340/7.54 |
| 6,142,929 | A * | 11/2000 | Padgett | 600/38 |
| 6,899,671 | B1 | 5/2005 | Fontenot | |
| 6,991,599 | B2 | 1/2006 | Hudson | |
| 7,513,868 | B1 | 4/2009 | Fontenot | |
| 8,313,424 | B2 | 11/2012 | Gabrielidis | |
| 8,639,360 | B2 | 1/2014 | Wise | |
| 2005/0187431 | A1 * | 8/2005 | Hudson | 600/38 |
| 2012/0323068 | A1 | 12/2012 | Atchinson et al. | |
| 2013/0019912 | A1 * | 1/2013 | Kennedy et al. | 135/16 |

OTHER PUBLICATIONS

The Antique Intruder Sex Machine, Retrieved on Aug. 12, 2014, <http://www.holisticwisdom.com/the-antique-intruder.htm.>, 1 page.
The Hammer Sex Machine, Retrieved on Aug. 12, 2014, <http://www.holisticwisdom.com/the-hammer.htm>, 1 page.
The Intruder Sex Machine, Retrieved on Aug. 12, 2014, <http://www.holisticwisdom.com/the-intruder.htm>, 1 page.
The Predator Sex Machine, Retrieved on Aug. 12, 2014, <http://www.holisticwisdom.com/the-predator.htm>, 1 page.
The Trespasser Sex Machine, Retrieved on Aug. 12, 2014, <http://www.holisticwisdom.com/the-trespasser.htm>, 1 page.

* cited by examiner

*Primary Examiner* — Samuel Gilbert
(74) *Attorney, Agent, or Firm* — Schmeiser, Olsen & Watts, LLP

(57) ABSTRACT

An apparatus and method for sexual stimulation that includes a handheld driving member and an insertive member that is tipped with an insertive sexual device that moves in response to a user's movement of the driving member. The two members are coupled by a rotating or tilting coupling mechanism with which a user may control the motion of the insertive device with great precision. The coupling device couples the driving member to the insertive member in such a way as to translate a movement of the driving member to an analogous movement of the insertive member that the two movements are equivalent or proportional in amplitude, acceleration, and velocity, but mechanically out of phase. Variations allow the apparatus to be used simultaneously by two users, or provide features by which a user may customize the scale or direction of the insertive device's motion.

17 Claims, 4 Drawing Sheets

PERSONAL APPARATUS FOR SEXUAL STIMULATION

TECHNICAL FIELD

This disclosure relates to an apparatus that allows one or more users to engage in sexual stimulation.

BACKGROUND

Devices that allow a user engage in personal sexual stimulation or self-stimulation range from small handheld objects, like dildos or vibrators, to complex, electrically powered machinery. Handheld objects are often limited in manner of use and may require a degree of dexterity or strength that makes them impractical or uncomfortable to certain people, such as the elderly or persons with physical handicaps. Mechanical and electrically powered devices may be operated autonomously or may require minimal hands-on control, but are generally large, heavy, expensive, or even potentially dangerous. There is thus a need for a flexible and safe stimulation device that offer a variety of user-selectable modes of operation and that is lightweight, compact, relatively inexpensive, and easy to store, set up, and use.

SUMMARY

All examples and features mentioned below can be combined in any technically possible way.

Disclosed is an apparatus for sexual stimulation that, in one aspect, includes:

a first movable coupling mechanism comprising a first set of two or more attachment points and a set of one or more support points, wherein the first set of two or more attachment points and the set of one or more support points each identify a distinct location on a surface of the first movable coupling mechanism;

a first driving member comprising a first end connected to a second end, wherein the first end is coupled to the first coupling mechanism at a first attachment point of the first set of two or more attachment points;

a first insertive member comprising a third end connected to a fourth end, wherein the third end is coupled to the first coupling mechanism at a second attachment point of the first set of two or more attachment points; and a support structure attached to the set of one or more support points so as to allow the first movable coupling mechanism to rotate about a first axis that passes through the first set of one or more support points in response to a movement of the first driving member.

Examples of this aspect may include combinations of the following features:

a handle affixed to the second end of the first driving member such that a user may manually move the first driving member;

a stimulating fixture affixed to the fourth end of the first insertive member such that a user may control motion of the stimulating fixture by manually moving the first driving member, and wherein the stimulating fixture is configured to provide sexual stimulation to the user;

a stimulating fixture that is an electrical or battery-powered device that is controlled by a controlling means comprised by the handle;

a stimulating fixture that is selected from a group comprising: a rigid, pliable, or flexible phallus; a cuff or sleeve; a suction device; a pump; a vibrating device; a device capable of applying electrical current to a user's body; and combinations thereof;

a first coupling mechanism that is a lever;

a first coupling mechanism that comprises at least part of a disk;

a first coupling mechanism that is constrained to limit its range of rotation;

a second driving member comprising a fifth end connected to a sixth end, wherein the fifth end is coupled to the first coupling mechanism at a third attachment point of the first set of two or more attachment points;

a second insertive member comprising a seventh end connected to an eighth end, wherein the seventh end is coupled to the first coupling mechanism at a fourth attachment point of the first set of two or more attachment points;

a first driving member that is fixed in length;

a first driving member that is completely or partially flexible;

an adjustable distance between the first end and the second end;

a first attachment point that comprises a set of driver-attachment positions configured to allow the user, while using the personal apparatus, to detach the first driving member from a first driver-attachment position of the set of driver-attachment positions and reattach the first driving member to a second driver-attachment position of the set of driver-attachment positions;

a support structure that comprises one or more suction cups;

a support structure that comprises one or more clamps;

a support structure that comprises one or more hook-and-loop fasteners;

a first attachment point and a second attachment point that are located on the surface of the coupling mechanism at opposite sides of the first set of one or more support points; and a coupling mechanism that is free to swivel about a vertical axis perpendicular to the first axis.

Further disclosed is a method for forming a personal stimulation apparatus comprising:

forming a movable coupling mechanism having a set of two or more attachment points and a set of one or more support points, wherein the set of two or more attachment points and the set of one or more support points each identify a distinct location on a surface of the movable coupling mechanism;

attaching to the coupling mechanism a driving member comprising a first end connected to a second end, wherein the first end is attached to the coupling mechanism at a first attachment point of the set of two or more attachment points;

attaching to the coupling mechanism a insertive member comprising a third end connected to a fourth end, wherein the third end is coupled to the coupling mechanism at a second attachment point of the set of two or more attachment points;

attaching a support structure to the set of one or more support points so as to allow the movable coupling mechanism to rotate about an axis that passes through the set of one or more support points in response to a movement of the driving member;

attaching a handle affixed to the second end of the driving member such that a user may manually move the driving member; and attaching a stimulating fixture affixed to the fourth end of the insertive member such that a user may control motion of the stimulating fixture by manually moving the driving member, and wherein the stimulating fixture is configured to provide sexual stimulation to the user, wherein the stimulating fixture is selected from a group comprising: a rigid, pliable, or flexible phallus; a cuff or sleeve; a suction device; a pump; a vibrating device; a device capable of applying electrical current to a user's body; and combinations thereof.

The above and further features and advantages may be better understood by referring to the following description in conjunction with the accompanying drawings, in which like numerals indicate like structural elements and features. The drawings are not necessarily to scale and are instead primarily intended to illustrate principles of features and implementations.

Other aspects and features and combinations of them can be expressed as methods, apparatus, systems, program products, means for performing functions, and in other ways.

DETAILED DESCRIPTION

Embodiments of the present invention comprise methods and apparatus by which a user may perform sexual stimulation by means of a remotely controlled insertive or thrusting action. These embodiments differ from existing methods and apparatus in that the present invention comprises a mechanism that empowers a user to perform sexual stimulation from a variety of angles and perspectives without requiring an electrically powered or battery powered drive mechanism. Such embodiments give the user great flexibility in choosing an operating position and perspective that is comfortable and convenient, regardless of whether the user lacks normal motor functions or strength, and regardless of whether the invention is used in a confined or otherwise constrained space.

Figure 1A:
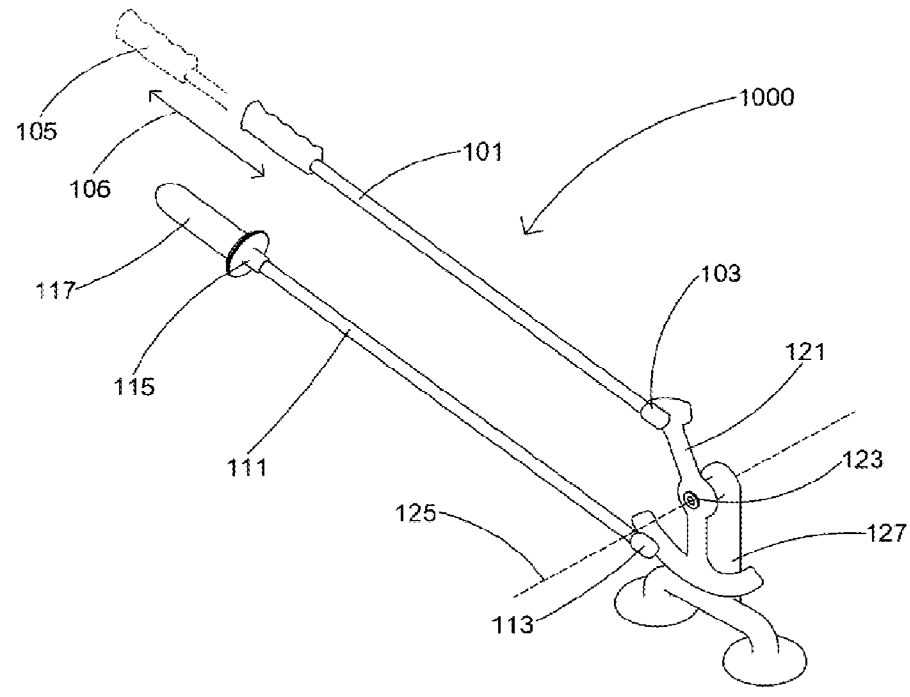
FIG. 1A is an isometric view of an embodiment of a personal apparatus for sexual stimulation 1000.

FIG. 1A is an isometric view of an embodiment of a personal apparatus for sexual stimulation 1000. FIG. 1A comprises items 1000 and 101-127.

A driving member 101 is coupled to a driven insertive member 111 through a movable coupling mechanism 121, such that a substantially linear movement of driving member 101 produces a corresponding rotational or tilting movement of coupling mechanism 121. This corresponding movement rotational or tilting movement in turn produces an analogous, substantially lateral, movement of insertive member 111, where a movement of insertive member 111 may be in a direction that is generally opposite of a direction of a related movement of driving member 101. This configuration allows a user, by moving driving member 101, to indirectly, but precisely, control excursion, velocity, acceleration, and force of a motion of insertive member 111.

FIG. 1A shows driving member 101 and driven insertive member 111 as elongated poles, but one or both of these members may take other forms that are capable of translating a thrusting or lateral movement of a user into a rotational or tilting motion of coupling mechanism 121, or of translating to a rotational or tilting movement of coupling mechanism 121 into a thrusting or lateral movement of insertive device or fixture 117 that is aligned such that a longitudinal axis of the insertive device or fixture 117 is essentially coaxial with a longitudinal axis of insertive member 111. Such other forms may include, but are not limited to, a rigid pole, tube, rod, or column; a collapsible or telescoping structure; a flexible or bendable structure; an articulated arm or armature; or a compound structure that comprises combinations thereof. In one example, a length of driving member 101 may be made adjustable in a direction shown by arrow 106 by means known to those skilled in the art, such as by implementing driving member 101 as a collapsible or telescoping pole.

In some embodiments, a distinct handle or grip 105 may be affixed to one end of driving member 101 by attachment means known to those skilled in the art. Such attachment means may permanently affix handle or grip 105 to driving member 101 or may allow attachment of interchangeable handles or grips to driving member 101. Examples of such known attachment means include, but are not limited to: glue, a pressure fitting, a weld, a molded fitting, a screw thread, and combinations thereof. Handle or grip 105 may be attached to driving member 101 either rigidly or with a degree of flexion.

Although FIG. 1A shows a handle or grip 105 configured to be grasped by hand, other embodiments may comprise alternate control mechanisms that may allow a user to move driving member 101 with an other part of the body or by means of other types of bodily motion. An embodiment may be configured, for example, with one or more of a pedal, cuff, bar, hook, glove, strap, or other interfacing entity that allows the personal apparatus 1000 to be operated by a user who lacks full use of her arms or hands.

An optional mounting means 115 may be affixed to one end of insertive member 111 in order to allow a device or fixture 117 to be attached to insertive member 111. In some embodiments, mounting means 115 may allow a fixture 117 to be permanently attached to insertive member 111, and in other embodiments, mounting means 115 may allow attachment of interchangeable fixtures 117 to insertive member 111. In embodiments in which a fixture 117 is an intrinsic part of insertive member 111, there may be no need for a distinct mounting means 115.

In some embodiments, fixture 117 may comprise either an insertive or non-insertive device. Such fixtures or devices 117 may include, but are not limited to: a rigid, pliable, or flexible phallus; a cuff or sleeve; a suction device; a pump; a vibrating device; a device capable of applying electrical current to a user; and combinations thereof In some embodiments, a handle or grip 105 may comprise a controlling means by which a user may control a value of a parameter associated with a fixture 117 or with an operation of the apparatus 100. If, for example, fixture 117 is an electrically powered device, a handle or grip 105 may allow a user to toggle power to device 117 by squeezing a grip, pressing a button, flicking a switch, sliding a lever, touching a sensor, completing an electrical circuit, or operating an other controlling means integrated into handle or grip 105.

In other embodiments, a controlling means of a handle or grip 105 may allow a user to vary a value of an operational parameter of a fixture 117. In one example, if fixture 117 is a variable-speed vibrating device, a controlling means integrated into a grip 105 may allow a user to control an intensity or frequency of fixture 117's vibrations by varying the user's gripping force, by rotating or tilting the grip through a certain angle, or by holding the grip for a particular duration of time. Many other functions and mechanisms are possible.

In yet other embodiments, a handle or grip 105 may allow a user to perform operations related to other functions or characteristics of apparatus 1000, such as setting a range of motion of a rotating coupling mechanism 121

Driving member 101 is attached to coupling mechanism 121 at a first attachment point 103 by any attachment means known to those skilled in the art of mechanical design, such that the attachment means allows a user to indirectly move coupling mechanism 121 by directly moving driving member 101.

Similarly, insertive member 111 is attached to coupling mechanism 121 at a second attachment point 113 by any attachment means known to those skilled in the art of mechanical design, such that the attachment means permits insertive member 111 to move in response to a movement of coupling mechanism 121.

The attachment means by which driving member 101 or insertive member 111 is attached to coupling mechanism 121 may comprise, but is not limited to, combinations of an axle, a nut, a bolt, a screw, a hinge, a pulley, a sprocket and chain, a cable or wire, an articulated member, or one or more bearings. In some embodiments, coupling mechanism 121 may comprise multiple sub-components that may provide alternate attachment locations or means. In some embodiments, coupling mechanism 121 may comprise more complex configurations, such, but not limited to, a set of multiple circular or noncircular gears that allow a user to alter responsiveness of the apparatus 1000 much like a bicycle derailleur allows a cyclist to alter a gear ratio of the bicycle's drive mechanism.

The coupling mechanism 121 is mounted to a support structure 127 at one or more support attachment points 123 by means known to those skilled in the art of mechanical design. In the embodiment of FIG. 1A, this attachment means allows coupling mechanism 121 to rotate around an axis of rotation 125, where the axis 125 passes through a support attachment point 123 and is perpendicular to the plane of the page in FIG. 1B. In some embodiments, a range of rotation of coupling mechanism may be restricted by any mechanical or electrical means known to those skilled in the art.

Figure 1B:
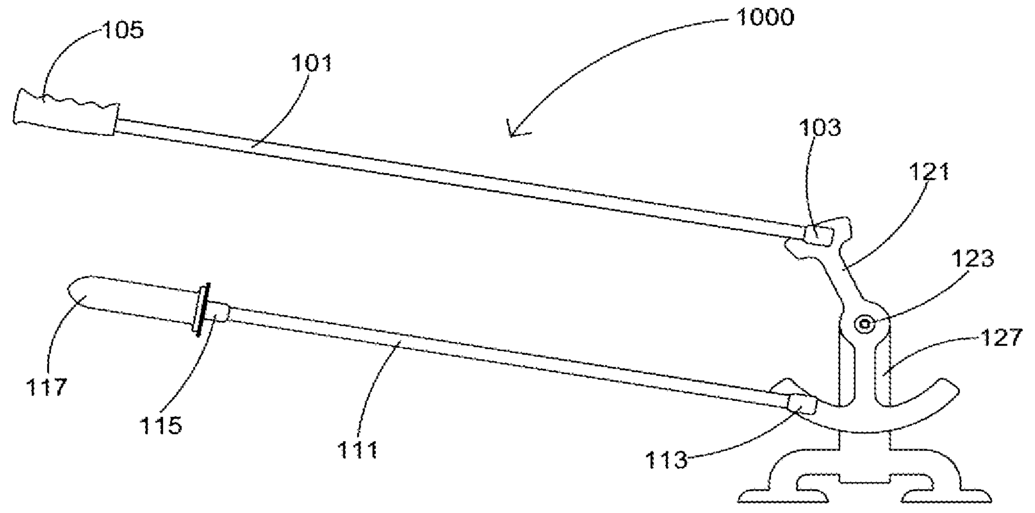
FIG. 1B is a side view of the embodiment of personal apparatus 1000 shown in FIG. 1A.

In embodiments shown in FIGS. 1A and 1B, the first attachment point 103 and the second attachment point 113 are positioned on coupling mechanism 121 on opposite sides of axis of rotation 125. Such an arrangement allows a user, by moving driving member 101 a first distance along a first direction, to rotate coupling mechanism 121 around axis 125 so as to move insertive member 111 a second distance along a second direction.

In embodiments shown in FIG. 1A and FIG. 1B, the driving motion of driving member 101 and the resulting analogous motion of insertive member 111 may be substantially equivalent in velocity, acceleration, and distance, but opposite in direction. This relationship between the driving motion and the analogous motion may vary in other embodiments.

When the first attachment point 103 and the second attachment 113 are equally distant from the axis of rotation 125, the coupling mechanism will move the insertive member 111 a distance that is substantially equal in magnitude to the magnitude of the distance that the user moved the driving member 101. The coupling mechanism will also reverse the direction of the insertive member 111, such that the movements of the driving member 101 and the insertive member 111 are synchronized, but 180 degrees out of phase. In such configurations, if a user thrusts the driving member 101 in a generally leftward direction, the insertive member 111 will thrust in a generally rightward direction.

In other embodiments, the first attachment point 103 and the second attachment 113 may not be equally distant from the axis of rotation 125. In such cases, a first movement of driving member 101 indirectly produces a second, analogous, movement of insertive member 111, where the magnitude of the distance of the second movement is proportional to, but not equal to, the magnitude of the distance of the first movement. As in the previous example, these two movements are synchronized in time, but mechanically out of phase.

In all embodiments, the above relationship between a distance of a first motion of driving member 101 and a distance of a resulting motion of insertive member 111 may be affected by the exact direction of the first motion. If, for example, a user holds the driving member 101 at an angle such that the driving member 101 and the insertive member 111 are not parallel, the two members may not move in exactly opposite directions and the distance of the resulting motion of the insertive member 111 may be a function of that angle, as is known to those skilled in the art of mechanical design or basic geometry.

Coupling mechanism 121 is attached to support structure 127 at one or more support attachment points 123 by any attachment means known to those skilled in the art. Support structure 127 may take any form or structure capable of firmly supporting apparatus 1000 and, in one example, is shown in FIG. 1A as a vertical support member connected to a suction-cup base that provides stability to personal apparatus 1000 by allowing apparatus 1000 to be firmly affixed to a smooth surface like a floor, door, or wall. One advantage of such a configuration is the resulting ability of apparatus 1000 to operate while mounted on a vertical, horizontal, or slanted surface. In another embodiment, a support structure 127 that comprises a clamp may allow the personal apparatus 1000 to be attached to the headboard of a bed.

Nore complex embodiments of support structure 127 may comprise other mounting means known in the art, such as a clamp, a hook-and-loop fastener (such as a "Velcro" strip), adhesive strips, or a weighted base. A support structure 127 might, for example, comprise several hook-and-loop strips designed to be attached to a separate flat plate outfitted with a complementary set of hook-and-loop fasteners. Such a mechanism might allow a user to temporarily or permanently affix the plate to a desired surface (such as a bedroom floor) and then attach the personal apparatus 1000 to the plate by means of the hook-and-loop fasteners whenever the apparatus 1000 is to be used.

Figure 4:
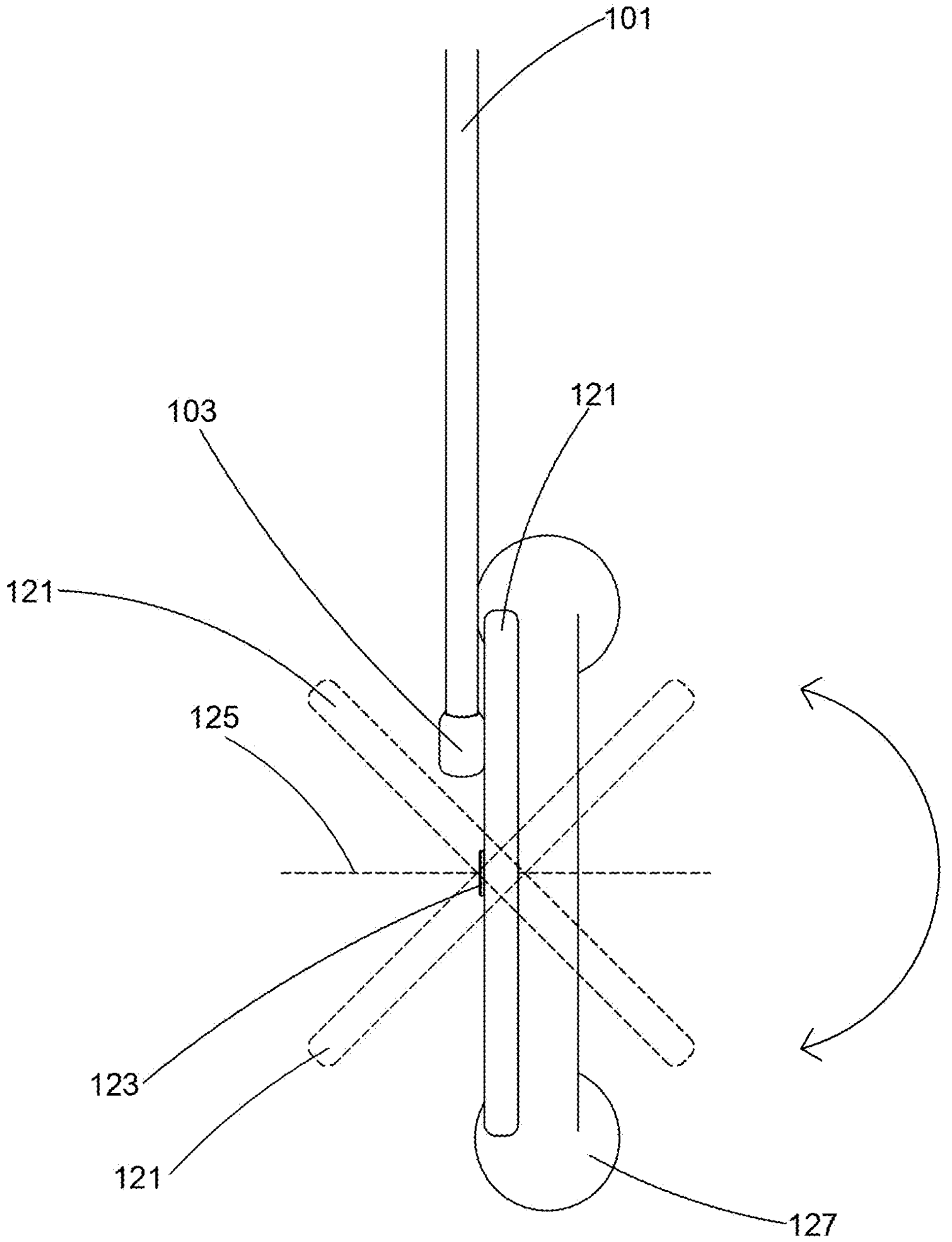
FIG. 4 is a top view of an embodiment of the present invention that comprises a coupling mechanism capable of swiveling around a vertical axis.

As shown in FIG. 4, support structure 127 may comprise movable components that allow driving member 101, insertive member 111, or coupling mechanism 121 to move with additional degrees of freedom. In some embodiments, support structure 127 may comprise guides or other constraints that limit or control a motion of driving member 101, insertive member 111, or coupling mechanism 121.

In other embodiments, support structure 127 may further support one or more auxiliary members that may each be tipped with a distinct insertive fixture, such as a second phallus. In this manner, a user may simultaneously insert or move insertive fixtures into multiple orifices. One such embodiment might, for example, comprise an auxiliary member that is substantially parallel to insertive member 111, and that is supports a second phallus that is not configured to move in response to a movement of coupling mechanism 121. Such an auxiliary member may comprise an articulated arm, an entirely or partially flexible elongated structure, a telescoping structure, combinations thereof, or an other means of supporting the second phallus in a fixed or user-adjustable position. In this example, a user might insert fixture 117 into a first orifice of the user and move it by means described above, while simultaneously manually moving the second phallus in a second orifice, through direct bodily movement. Here, the user could position the second phallus for comfortable insertion by manually bending, shaping, twisting, rotating, or otherwise positioning the auxiliary member.

Many other similar configurations are possible that comprise one or more additional fixtures positioned and held in place by one or more auxiliary members that may not be moved by the coupling mechanism 121.

FIG. 1B is a side view of the embodiment of personal apparatus 1000 shown in FIG. 1A. FIG. 1B comprises items 1000 and 101-127.

Items identified by reference numerals 1000 and 100-127 in FIG. 1B are similar in scope and function to items identified by corresponding reference numerals in FIG. 1B. Because axis of rotation 125 is perpendicular to the plane of the page of FIG. 1B, axis 125 is not visible in this figure.

Figure 2A:
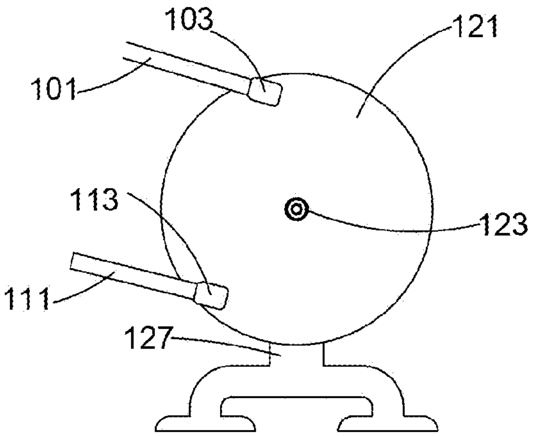
FIG. 2A shows an embodiment of the present invention that comprises a disk-shaped coupling mechanism.
Figure 2B:
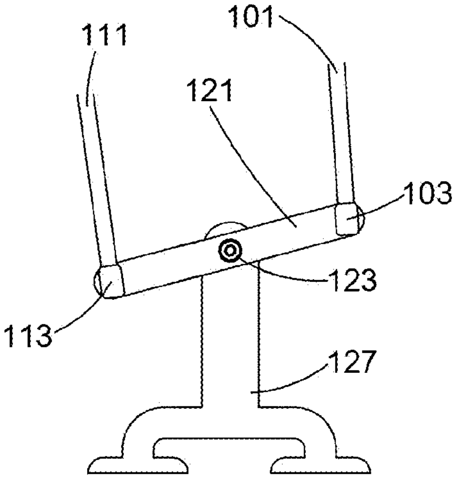
FIG. 2B shows an embodiment of the present invention that comprises a lever coupling mechanism.
Figure 2C:
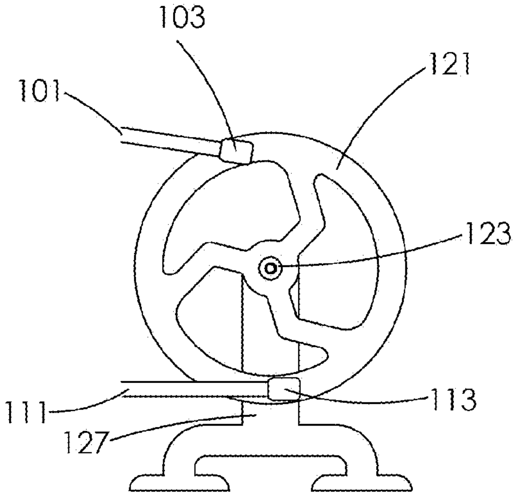
FIG. 2C shows an embodiment of the present invention that comprises a rotating wheel-, ring-, or cylinder-shaped coupling mechanism.

Although FIG. 1A shows coupling mechanism 121 as a circular lever, this should not be construed to limit the form or structure of coupling mechanism 121. As illustrated by FIGS. 2A-2C, coupling mechanism 121 may comprise any shape or structure, or be comprised of any sub-components or material composition, that is allows it to perform the functions described herein.

In FIGS. 2A-2C, items labeled with reference numerals 101, 103, 111, 113, 123, and 127 are similar in form and function to similarly labeled items in FIG. 1A.

FIG. 2A shows an embodiment in which coupling mechanism 121 takes the form of a disk attached to support member 127 at a support attachment point 123 located at the center of the disk, and further attached to members 101 and 111 at attachment points 103 and 113 located along or just within the circumference of the disk. These attachment points may be located 180 degrees apart, along two other points on a diameter of the disk, or in other locations. In one example, the points may be located 120 degrees apart on circle centered around support attachment point 123. Many other possible locations are possible, and may be chosen as a function of a design goal of a particular embodiment of the present invention.

FIG. 2B shows an embodiment in which coupling mechanism 121 comprises a straight or curved bar or plate, or some other lever-like device, that is attached to members 101 and 111 at attachment points 103 and 113 located at points on coupling mechanism 121 that are on opposite sides of support attachment point 123, and that is further mounted to support member 127 at support attachment point 123. In this example, support attachment point 123 is located near the center of the coupling mechanism 121, roughly equidistant between attachment points 103 and 113, but in other embodiments, other points of placement may be chosen, so long as they permit apparatus 1000 to operate in a manner described herein.

FIG. 2C shows an example of a class of embodiments in which coupling mechanism 121 is a wheel, ring, cylinder, or any other shape that can be rotated around an axis by a force exerted at one end of the mechanism 121, in order to apply force to an object attached to the other end of the mechanism 121. In related embodiments, the outer rim of such a coupling mechanism 121 may not extend through an entire 360-degree arc shown in FIG. 2C and may instead, as shown in an example of FIG. 1A, extend only through a portion of the 360-degree range.

FIGS. 2A-2C should not be construed to show every possible configuration of coupling mechanism 121. Many other variations are possible, as shown, for example, in FIG. 4, and some variations may alter the coupling function of mechanism 121, constrain its motion, or provide additional degrees of freedom to the motion of mechanism 121.

Coupling mechanism 121 might, for example, comprise a sprocket or gear over which is laid a chain and chain guard that operate like a drive mechanism of a bicycle or motorcycle. In such an embodiment, driving member 101 and insertive member 111 might be connected to opposite ends of a chain that engages teeth of sprocket 121, and an end of member 101 or 111 that is closest to the coupling mechanism 121 may be curved or flexible in order to facilitate effective operation of such a mechanism. In a similar embodiment, a cable might be strung across the outer edge of a disc-shaped coupling mechanism 121, wherein a cross-section of the outer edge of coupling mechanism 121 has a concave shape, notches, straps, or other means tailored to hold the cable in place along the edge of the coupling-mechanism disc.

In yet other embodiments, coupling mechanism 121 might comprise an asymmetric gear or might comprise multiple gears. A coupling mechanism 121 that comprises an asymmetric cog, sprocket, or gear, for example, may allow a distance between the axis of rotation 125 and an attachment point 103 or 113 to vary as the coupling mechanism rotates, thus providing an advantage to a user by allowing more subtle control of an insertive device or fixture 117 at certain depths of insertion. In one example, a movement of driving member 101 when coupling mechanism 121 is in a first position might move insertive member 111 twice as far as would a similar movement of driving member 101 when coupling mechanism 121 is at a second position.

Figure 3A:
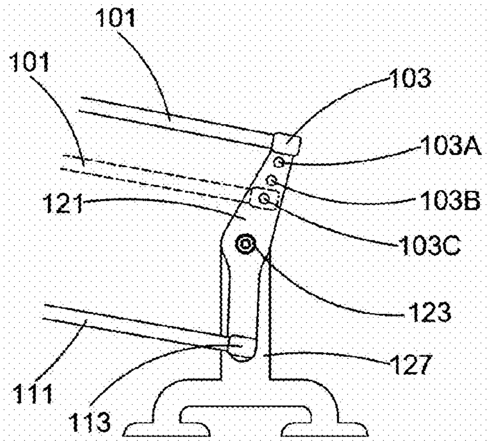
FIG. 3A shows an embodiment of the present invention that comprises multiple points of attachment for a driving member.

FIG. 3A shows an embodiment of the present invention that comprises multiple points of attachment for the driving member 101.

Items identified by reference numerals 101, 103, 111, 113, 121, 123, and 127 are similar in scope and function to items identified by corresponding reference numerals in FIG. 1A.

As in FIG. 1A and FIG. 1B, driving member 101 may be attached to coupling mechanism 121 at a first attachment point 103 by any attachment means known to those skilled in the art of mechanical design, such that the attachment means allows a user to rotate or tilt coupling mechanism 121 by moving driving member 101.

Here, however, coupling mechanism 121 comprises three additional points of attachment 103A, 103B, and 103C, each of which may be selected by a user as a point of attachment for driving member 101. In one example, the dotted outline of driving member 101 in FIG. 3A shows a position of driving member 101 if driving member 101 were to be attached to coupling mechanism 121 at attachment point 103C.

In the embodiment shown in FIG. 3A, the four points of attachment 103-103C allow a user to select a radius of rotation associated with a rotation of coupling mechanism 121 in response to a movement of driving member 101. In this example, the radius of rotation is a distance between the center of the rotating coupling mechanism 121 and a point of attachment 103, 103A, 103B, or 103C.

Because innermost point of attachment 103C is closer to the center point of coupling mechanism 121 than is outermost point of attachment 103, attaching the driving member 101 to point of attachment 103C creates a mechanical system that has a smaller radius of rotation than would exist when driving member 101 is attached to outermost point of attachment 103. Thus, a movement of driving member 101 would rotate coupling mechanism 121 through a greater angle if member 101 is attached at point 103C than it would if member 101 were attached at point 103.

In this example, alternate points of attachment are arranged along a single radius of coupling mechanism 121, but in other embodiments, points of attachment may be skewed, staggered, or arranged in an other configuration that might give a user control over responsiveness, scale, rigidity, or an other parameter of a motion of the insertive member 111 in response to a motion of the driving member 101. In other embodiments, coupling mechanism 121 may be associated with more than four or less than four possible points of attachment for driving member 101.

As with all features illustrated in FIGS. 2A-2C and FIGS. 3A-3D, the alternate points of attachment shown in FIG. 3A may be combined in any practical way, using any mechanical means known to those skilled in the art, with other features of embodiments of FIGS. 2A-2C and FIGS. 3A-3D.

Figure 3B:
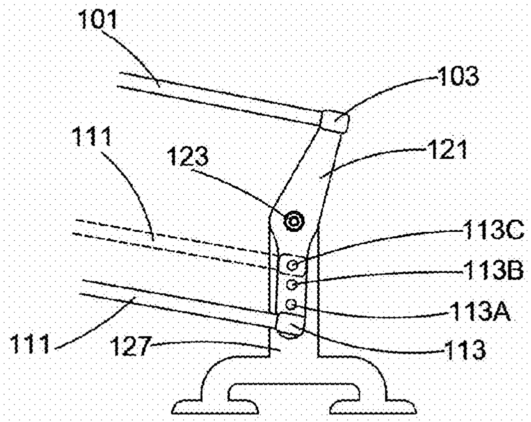
FIG. 3B shows an embodiment of the present invention that comprises multiple points of attachment for an insertive member.

FIG. 3B shows an embodiment of the present invention that comprises multiple points of attachment for the insertive member 111.

Items identified by reference numerals 101, 103, 111, 113, 121, 123, and 127 are similar in scope and function to items identified by corresponding reference numerals in FIG. 1A.

As in FIG. 1A and FIG. 1B, insertive member 111 may be attached to coupling mechanism 121 at a second attachment point 113 by any attachment means known to those skilled in the art of mechanical design, such that the attachment means allows a rotational or tilting movement of coupling mechanism 121 to move insertive member 111.

Here, however, coupling mechanism 121 comprises three additional points of attachment 113A, 113B, and 113C, each of which may be selected by a user as a point of attachment for insertive member 111. In one example, the dotted outline of driving member 111 in FIG. 3B shows a position of driving member 111 if driving member 111 were to be attached to coupling mechanism 121 at attachment point 113C.

In the embodiment shown in FIG. 3B, the four points of attachment 113-113C allow a user to select a radius of rotation associated with the degree of movement of insertive member 111 in response to a rotating or tilting movement of coupling mechanism 121 about axis of rotation 125. In this example, the radius of rotation is a distance between the center 123 of rotating coupling mechanism 121 and a point of attachment 113, 113A, 113B, or 113C.

Because innermost point of attachment 113C is closer to the center point of coupling mechanism 121 than is outermost point of attachment 113, attaching insertive member 111 to point of attachment 113C creates a mechanical system that has a smaller radius of rotation than would exist if insertive member 111 was attached to outermost point of attachment 113. Thus, a rotation or tilting motion of coupling mechanism 121 would cause a smaller movement of insertive member 111 when member 111 is attached at point 113C than it would when member 111 were attached at point 113.

In this example, alternate points of attachment are arranged along a single radius of coupling mechanism 121, but in other embodiments, points of attachment may be skewed, staggered, or arranged in an other configuration that might give a user control over responsiveness, scale, rigidity, or an other parameter of a motion of the insertive member 111 in response to a motion of driving member 101. In other embodiments, coupling mechanism 121 may be associated with more than four or less than four possible points of attachment for insertive member 111.

As with all features illustrated in FIGS. 2A-2C and FIGS. 3A-3D, the alternate points of attachment shown in FIG. 3B may be combined in any practical way, using any mechanical means known to those skilled in the art, with other features of embodiments of FIGS. 2A-2C and FIGS. 3A-3D.

Many other variations of these basic embodiments are possible, and the scope of the present invention should not be construed to be limited to embodiments shown in FIGS. 1-4. In one embodiment not shown in the figures, for example, a second device or fixture, similar to the first device or fixture 117 described above, may be attached to support structure 127 by means of a flexible or jointed support structure, such as a gooseneck appendage or an articulated arm not attached to the coupling mechanism 121. Such a configuration might allow a user to comfortably insert the second device or fixture into a first orifice of the user's body, and then allow the embodiment to continue to support the inserted second device or fixture while the user inserts and moves the first device or fixture 117 in a second orifice by means of any of the mechanisms described above.

In such embodiments, this second device or fixture may comprise any insertive or non-insertive device known to those skilled in the art. Such fixtures or devices 117 may be insertive or non-insertive and may include, but are not limited to: a rigid, pliable, or flexible phallus; a cuff or sleeve; a suction device; a pump; a vibrating device; a device capable of applying electrical current to a user; and combinations thereof.

Other embodiments are possible within the scope of the present invention, where such embodiments augment the coupled user-control mechanism described in FIGS. 1-4 with additional mechanisms; mounted devices; fixed, flexible, or movable attachments; or other auxiliary stimulating means.

Figure 3C:
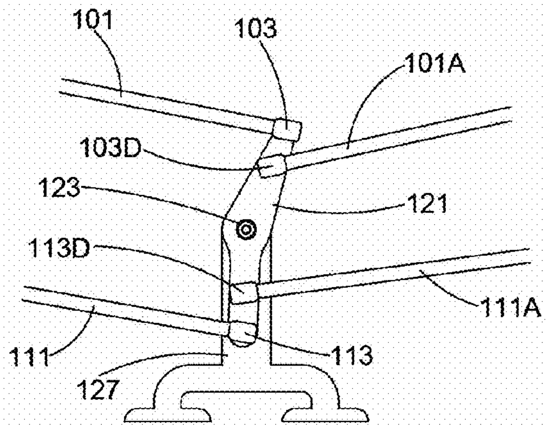
FIG. 3C shows an embodiment of the present invention that comprises multiple points of attachment capable of accommodating two driving-member/insertive-member pairs.

FIG. 3C shows an embodiment of the present invention that comprises multiple points of attachment for two pairs of driving members and insertive members.

Items identified by reference numerals 101, 103, 111, 113, 121, 123, and 127 are similar in scope and function to items identified by corresponding reference numerals in FIG. 1A.

As in FIG. 1A and FIG. 1B, driving member 101 may be attached to coupling mechanism 121 at a first attachment point 103 by any attachment means known to those skilled in the art of mechanical design, such that the attachment means allows a user to rotate or tilt coupling mechanism 121 by moving driving member 101.

As in FIG. 1A and FIG. 1B, insertive member 111 may be attached to coupling mechanism 121 at a second attachment point 113 by any attachment means known to those skilled in the art of mechanical design, such that the attachment means allows a movement of coupling mechanism 121 to in turn move insertive member 111.

Here, however, coupling mechanism 121 may comprise either one or both of: an additional point of attachment 103D to which may be attached a second driving member 101A; and an additional point of attachment 113D to which may be attached a second driving member 111A.

This ability to attach a second driving member 101A or a second insertive member 111A, or both, allows this embodiment of the personal apparatus to accommodate two concurrent or simultaneous users. When two driving members 101 and 101A are attached to the coupling mechanism, the two users may take turns controlling the motion of the coupling mechanism 121 or may concurrently share control of the coupling mechanism 121. When two insertive members 111 and 111A are attached to the coupling mechanism in this manner, the two users may each enjoy sexual stimulation controlled by a motion of either of the two insertive members 111 and 111A.

In some embodiments, one or more of the driving or insertive members may be attached so as to allow the one or more driving or insertive members to swivel in one or more directions. This feature might allow tandem users, when using the apparatus, greater flexibility in positioning their bodies relative to each other, or relative to other objects in their environment.

In some embodiments, points of attachment 103 and 103D may be positioned so as to create distinct mechanical systems, in conjunction with coupling mechanism 121, that each have a distinct or different radius of rotation. Selecting a radius of rotation may, as explained above in the description of FIG. 3B, give each user a different degree of responsiveness, scale, or rigidity, when using the apparatus.

In this example, points of attachment are shown to be arranged along a single radius of the coupling mechanism, but in other embodiments, points of attachment may be skewed, staggered, or arranged in an other configuration that might give a user control over responsiveness, scale, rigidity, or an other parameter of a motion of the insertive member 111 in response to a motion of the insertive member 111.

As with all features illustrated in FIGS. 2A-2C and FIGS. 3A-3D, the alternate points of attachment shown in FIG. 3C may be combined in any practical way, using any mechanical means known to those skilled in the art, with other features of embodiments of FIGS. 2A-2C and FIGS. 3A-3D.

Figure 3D:
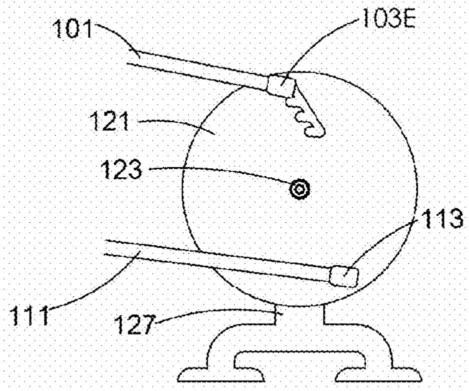
FIG. 3D shows an embodiment of the present invention that allows a user to vary a point of attachment of the driving member while using the apparatus.

FIG. 3D shows an embodiment of the present invention in which a user may vary a point of attachment of driving member 101 while using the embodiment.

Items identified by reference numerals 101, 111, 113, 121, 123, and 127 are similar in scope and function to items identified by corresponding reference numerals in FIG. 1A.

Here, however, driving member 101 is attached to coupling mechanism 121 at a first point of attachment 103E that comprises a "hook slot" aperture. This aperture may allow a user to attach driving member 101 to coupling mechanism 121 at any of a set of attachment points by lifting and sliding driving member 101 so as to inserts an end of driving member 101 into one of the aperture's hook slots. In other embodiments, the aperture may take an other shape that is known to those skilled in the art to allow an object, by means of physical movement of the object, to be physically locked into a location, lifted out of that location, moved to a different location, and then locked into that different location.

Because the user may choose a slot at any time by varying a direction of motion of driving member 101, the hook slot point of attachment 103E allows the user to change the point of attachment of driving member 101 ad hoc, in real time, while the user is actually using the apparatus to provide sexual stimulation.

The shape and orientation of the aperture may further be configured in any way that allows a user to reposition driving member 101 on-the-fly during actual usage of the apparatus 1000. In some embodiments, a user's choice of slot may allow the user to vary the radius of rotation of the apparatus, the distance between the user and the apparatus, the vertical height of the attachment point, or other parameters.

As with all features illustrated in FIGS. 2A-2C and FIGS. 3A-3D, the ook slot point of attachment 103E element unique to the embodiment of FIG. 3D may be combined in any practical way, using any mechanical means known to those skilled in the art, with other features of embodiments of FIGS. 2A-2C and FIGS. 3A-3D. For example, although coupling mechanism 121 is shown in FIG. 3D as a disk, other features of FIG. 3D may be combined with any other form or structure of coupling mechanism 121 shown in FIGS. 2A-2C or otherwise described herein.

FIG. 4 is a top view of an embodiment of the present invention that comprises a coupling mechanism 121 capable of swiveling around a vertical axis perpendicular to the axis of rotation 125. In FIG. 4, this vertical axis is perpendicular to the plane of the page.

Items identified by reference numerals 101, 103, 123, 125, and 127 are similar in scope and function to items identified by corresponding reference numerals in FIG. 1A.

Here, however, coupling mechanism 121, generally similar in scope and function to coupling mechanism 121 of FIG. 1A, is free to swivel about a vertical axis perpendicular to the axis of rotation 125. Two possible swiveled positions of coupling mechanism 121 are shown in FIG. 4 as dotted outlines.

Coupling mechanism 121 may be configured to both rotate about axis of rotation 125, as shown in FIG. 1A, and swivel through the vertical axis by any means known to those skilled in the art. One exemplary method would be to configure support structure 127 to comprise a vertical rod or pole attached to coupling mechanism 121 at or near support point of attachment 123 by means of an axle oriented along the axis of rotation 125 and passing both through the vertical rod or rod and through coupling mechanism 121 at support attachment point 123. If such a vertical rod or pole could itself rotate on its own vertical axis, coupling mechanism 121 would thus be able to both rotate on the axle about point 123 (as shown in FIG. 1A), and also swivel along with the vertical rod or pole when the vertical rod or pole is rotated about the vertical axis.

In another embodiment, support structure 127 might comprise a vertically oriented flat plate that may rotate about the vertical axis, relative to the lower portion of support 127. Many other support methods, known to those skilled in the art, may be configured in order to allow coupling mechanism 121 to swivel.

In various embodiments, coupling mechanism 121 may be free to swivel through a full 360-degree range of motion or may be constrained to swivel only through a certain number of degrees of arc. In some embodiments, a user may be able to manually set the range of swiveling motion. In some embodiments, coupling mechanism 121 may be free to further rotate in one or more other planes, or with one or more other degrees of freedom, by means of mechanical couplings similar to those described above.

As with all features illustrated in FIGS. 2A-2C and FIGS. 3A-3D, the ability of coupling mechanism 121 to swivel, as shown in FIG. 4, may be combined in any practical way, using any mechanical means known to those skilled in the art, with other features of embodiments shown in FIGS. 2A-2C and FIGS. 3A-3D.

The foregoing descriptions and figures are intended to illustrate and not to limit the scope of subject matter defined by the claims. Accordingly, it will be understood that additional modifications may be made without departing from the scope of the inventive concepts described herein and that other examples fall within the scope of the following claims.

The invention claimed is:

1. A personal stimulation apparatus comprising:

a first movable coupling mechanism comprising a first set of two or more attachment points and a support point, wherein the first set of two or more attachment points and the support point each identify a distinct location on a surface of the first movable coupling mechanism;

a first driving member comprising a first end connected to a second end, wherein the first end is coupled to the first coupling mechanism at a first attachment point of the first set of two or more attachment points, and wherein the distance between the first end and the second end is adjustable;

a first insertive member comprising a third end connected to a fourth end, wherein the third end is coupled to the first coupling mechanism at a second attachment point of the first set of two or more attachment points;

a support structure attached to the support point so as to allow the first movable coupling mechanism to rotate about a first axis that passes through the support point in response to a movement of the first driving member;

a handle affixed to the second end of the first driving member such that a user may manually move the first driving member; and a stimulating fixture affixed to the fourth end of the first insertive member such that a longitudinal axis of the stimulating fixture is essentially coaxial with a longitudinal axis of the first insertive member, and such that a user may control motion of the stimulating fixture by manually moving the first driving member, and wherein the stimulating fixture is configured to allow the user to provide sexual stimulation to the user.

2. The personal apparatus of claim 1, wherein the stimulating fixture is an electrical or battery-powered device that is controlled by a controlling means comprised by the handle.

3. The personal apparatus of claim 1, wherein the stimulating fixture is selected from a group comprising: a rigid, pliable, or flexible phallus; a cuff or sleeve; a suction device; a pump; a vibrating device; a device capable of applying electrical current to a user's body; and combinations thereof.

4. The personal apparatus of claim 1, wherein the first coupling mechanism is a lever.

5. The personal apparatus of claim 1, wherein the first coupling mechanism comprises at least part of a disk.

6. The personal apparatus of claim 1, wherein the first coupling mechanism is constrained to limit its range of rotation.

7. The personal apparatus of claim 1, further comprising:

a second driving member comprising a fifth end connected to a sixth end, wherein the fifth end is coupled to the first coupling mechanism at a third attachment point of the first set of two or more attachment points.

8. The personal apparatus of claim 1, further comprising:

a second insertive member comprising a fifth end connected to a sixth end, wherein the fifth end is coupled to the first coupling mechanism at a fourth attachment point of the first set of two or more attachment points.

9. The personal apparatus of claim 1, wherein the first driving member is completely or partially flexible.

10. The personal apparatus of claim 1, wherein the first attachment point comprises a set of driver-attachment positions configured to allow the user, while using the personal apparatus, to detach the first driving member from a first driver-attachment position of the set of driver-attachment positions and reattach the first driving member to a second driver-attachment position of the set of driver-attachment positions.

11. The personal apparatus of claim 1, wherein the support structure comprises one or more suction cups.

12. The personal apparatus of claim 1, wherein the support structure comprises one or more clamps.

13. The personal apparatus of claim 1, wherein the support structure comprises one or more hook-and-loop fasteners.

14. The personal apparatus of claim 1, wherein the first attachment point and the second attachment point are located on the surface of the coupling mechanism at opposite sides of the support point.

15. The personal apparatus of claim 1, wherein the coupling mechanism is connected to the support structure by a vertical support member that is free to rotate about a vertical axis perpendicular to the first axis such that the coupling mechanism is free to swivel about the vertical axis.

16. A method for forming a personal stimulation apparatus comprising:

forming a movable coupling mechanism having a set of two or more attachment points and a support point, wherein the set of two or more attachment points and the support point identifies a distinct location on a surface of the movable coupling mechanism;

attaching to the coupling mechanism a driving member comprising a first end connected to a second end, wherein the first end is attached to the coupling mechanism at a first attachment point of the set of two or more attachment points, and wherein the distance between the first end and the second end is adjustable;

attaching to the coupling mechanism an insertive member comprising a third end connected to a fourth end, wherein the third end is coupled to the coupling mechanism at a second attachment point of the set of two or more attachment points;

attaching a support structure to the support point so as to allow the movable coupling mechanism to rotate about an axis that passes through the support point in response to a movement of the driving member;

attaching a handle affixed to the second end of the driving member such that a user may manually move the driving member; and attaching a stimulating fixture affixed to the fourth end of the insertive member such that a longitudinal axis of the stimulating fixture is essentially coaxial with a longitudinal axis of the first insertive member, and such that a user may control motion of the stimulating fixture by manually moving the driving member, and wherein the stimulating fixture is configured to allow the user to provide sexual stimulation to the user, and wherein the stimulating fixture is selected from a group comprising: a rigid, pliable, or flexible phallus; a cuff or sleeve; a suction device; a pump; a vibrating device; a device capable of applying electrical current to a user's body; and combinations thereof.

17. A personal stimulation apparatus comprising:

a first movable coupling mechanism comprising a first set of two or more attachment points and a support point, wherein the first set of two or more attachment points and the support point each identify a distinct location on a surface of the first movable coupling mechanism;

a first driving member comprising a first end connected to a second end, wherein the first end is coupled to the first coupling mechanism at a first attachment point of the first set of two or more attachment points;

a first insertive member comprising a third end connected to a fourth end, wherein the third end is coupled to the first coupling mechanism at a second attachment point of the first set of two or more attachment points;

a support structure attached to the support point so as to allow the first movable coupling mechanism to rotate about a first axis that passes through the support point in response to a movement of the first driving member, wherein the support structure comprises one or more suction cups, clamps, or hook-and-loop fasteners a handle affixed to the second end of the first driving member such that a user may manually move the first driving member; and a stimulating fixture affixed to the fourth end of the first insertive member such that a longitudinal axis of the stimulating fixture is essentially coaxial with a longitudinal axis of the first insertive member, and such that a user may control motion of the stimulating fixture by manually moving the first driving member, and wherein the stimulating fixture is configured to allow the user to provide sexual stimulation to the user.

* * * * *